United States Patent
Lo et al.

(10) Patent No.: US 10,231,742 B2
(45) Date of Patent: Mar. 19, 2019

(54) SURGICAL DRILL

(71) Applicant: Soteria Industries Inc., Calgary (CA)

(72) Inventors: Ian K. Lo, Calgary (CA); Paul Sciore, Calgary (CA); Ken Muldrew, Calgary (CA)

(73) Assignee: SOTERIA INDUSTRIES, INC., Alberta (CA)

( * ) Notice: Subject to any disclaimer, the term of this patent is extended or adjusted under 35 U.S.C. 154(b) by 445 days.

(21) Appl. No.: 15/003,399

(22) Filed: Jan. 21, 2016

(65) Prior Publication Data
US 2016/0206328 A1   Jul. 21, 2016

Related U.S. Application Data

(60) Provisional application No. 62/106,061, filed on Jan. 21, 2015.

(51) Int. Cl.
*A61B 17/16* (2006.01)
*A61B 17/00* (2006.01)

(52) U.S. Cl.
CPC ...... *A61B 17/1626* (2013.01); *A61B 17/1622* (2013.01); *A61B 17/1624* (2013.01); *A61B 17/1628* (2013.01); *A61B 2017/00376* (2013.01); *A61B 2017/00424* (2013.01)

(58) Field of Classification Search
CPC ............ A61B 17/1622; A61B 17/1624; A61B 17/1626; A61B 17/1628; Y10T 408/23; Y10T 408/18; Y10T 408/17; Y10T 408/173
USPC ........................................................ 606/80
See application file for complete search history.

(56) References Cited

U.S. PATENT DOCUMENTS

| | | | | |
|---|---|---|---|---|
| 5,207,697 A | * | 5/1993 | Carusillo | A61B 17/1626 320/115 |
| 5,747,953 A | * | 5/1998 | Philipp | A61B 17/1626 318/114 |
| 2009/0245956 A1 | * | 10/2009 | Apkarian | A61B 17/1626 408/1 R |

(Continued)

FOREIGN PATENT DOCUMENTS

RU     2465847 C1    11/2012
WO   WO 2009/117836   10/2009

(Continued)

OTHER PUBLICATIONS

International Search Report and Written Opinion for PCT/IB2016/000097, dated Jun. 28, 2016.

*Primary Examiner* — Matthew J Lawson
*Assistant Examiner* — Amy R Sipp
(74) *Attorney, Agent, or Firm* — Bryan D. Zerhusen, Esq.; Cantor Colburn LLP

(57) ABSTRACT

In at least one aspect of this disclosure, a surgical drill can include a housing, a retracting enclosure slidably disposed within the housing and configured to move between an extended position and a retracted position and a retracting motor operatively connected to the retracting enclosure to move the retracting enclosure between the extended position and the retracted position. The drill can further include a drill motor including a motor shaft configured to connect to a drill chuck and disposed within the retracting enclosure such that the motor shaft can rotate relative to the retracting enclosure.

12 Claims, 3 Drawing Sheets

(56) References Cited

U.S. PATENT DOCUMENTS

2009/0326537 A1* 12/2009 Anderson .......... A61B 17/1624
606/80
2011/0245833 A1* 10/2011 Anderson ............... B23B 49/02
606/80
2013/0304069 A1* 11/2013 Bono ................. A61B 17/1624
606/80

FOREIGN PATENT DOCUMENTS

| WO | WO 2009/158115 | 12/2009 |
| WO | WO 2011/123703 | 10/2011 |
| WO | 2015006296 | 1/2015 |

\* cited by examiner

SURGICAL DRILL

RELATED APPLICATION

This application is related to and claims the benefit of the priority of U.S. Provisional Application 62/106,061, filed on Jan. 21, 2015, which is incorporated herein, by reference in its entirety.

FIELD OF THE INVENTION

The present disclosure relates to surgical drills, more specifically to drills with control systems.

BACKGROUND

During orthopedic surgery, when drilling through bone, it is important that the drill tip does not break through the distal cortex wall and damage any underlying soft tissue behind the bone. Drill tip penetration past the far cortex wall is known as "plunging" and the distance that the drill tip moves past the cortex is the "plunge depth." Traditional drilling systems commonly lead to plunging.

Such conventional methods and systems have generally been considered satisfactory for their intended purpose. However, there is still a need in the art for drills having enhanced controls for reducing or avoiding plunging. The present disclosure provides a solution for this need.

SUMMARY

In at least one aspect of this disclosure, a surgical drill can include a housing, a retracting enclosure slidably disposed within the housing and configured to move between an extended position and a retracted position and a retracting motor operatively connected to the retracting enclosure to move the retracting enclosure between the extended position and the retracted position. The drill can further include a drill motor including a motor shaft configured to connect to a drill chuck and disposed within the retracting enclosure such that the motor shaft can rotate relative to the retracting enclosure.

In certain embodiments, the drill can include a trigger switch configured to allow electrical energy to selectively flow to the retracting motor or the drill motor, a forward drill trigger operatively connected to the trigger switch, and a reverse drill trigger operatively connected to the trigger switch. The trigger switch can be configured to activate the drill motor in a first rotational direction when only the forward drill trigger is actuated. The trigger switch can be configured to activate the drill motor in a reverse direction relative to the first rotational direction when only the reverse drill trigger is actuated. In certain embodiments, when both the forward drill trigger and the reverse drill trigger are actuated simultaneously, the trigger switch can be configured to actuate the retracting motor to move the retracting enclosure from the extended position to the retracted position.

The reverse drill trigger can be disposed below the forward drill trigger such that a user can operate the forward drill trigger with an index finger and the reverse drill trigger with a middle finger.

The drill can include a feedback system and feedback display configured to display one or more parameters, graphs, gauges. The one or more parameters, graphs, and/or gauges can include drill motor torque, drill force, drill speed, time elapsed, depth verse time, drill motor current draw, power consumption, feed rate, temperature, sound, battery life, and/or a position of the retracting enclosure.

In certain embodiments, a speaker configured to make an audible noise when a drill bit connected to the drill motor is through a first layer to avoid plunging. The first layer can be a cortical bone layer.

The retracting enclosure can be connected to a rack to slide the retracting enclosure between the retracted position and the extended position, the rack operatively connected to a pinion. The retracting motor can be operatively connected to a helical worm gear to rotate the helical worm gear, wherein the helical worm gear is operatively connected to the pinion such that when the helical worm gear rotates, the pinion is rotated thereby which, in turn, moves the rack linearly.

In certain embodiments, the retracting motor can be configured to apply a force equal to or greater than a drill force to prevent the retracting enclosure from moving due to drill force. At least one of the retracting motor or the drill motor can be operatively connected to a reduction gear box.

The drill can further include a battery operatively connected to the drill motor and/or the retracting motor. The drill can also include a drill chuck operatively coupled to the drill motor, the drill chuck configured to selectively retain a drill bit.

In certain embodiments, a surgical drill can include a retracting enclosure slidably disposed within the housing and configured to move between an extended position and a retracted position, a retracting motor operatively connected to the retracting enclosure to move the retracting enclosure between the extended position and the retracted position, a drill motor including a motor shaft configured to connect to a drill chuck and disposed within the retracting enclosure such that the motor shaft can rotate relative to the retracting enclosure, a drill trigger configured to activate the drill motor in one or more rotation directions, and a retracting trigger configured to active the retracting motor to move the retracting enclosure from the extended position to the retracted position. The retracting trigger can be disposed below the forward drill trigger such that a user can operate the drill trigger with an index finger and the retracting trigger with a middle finger.

The drill can include a feedback system and feedback display configured to display one or more parameters, graphs, gauges. The one or more parameters, graphs, and/or gauges include drill motor torque, drill force, drill speed, time elapsed, depth verse time, drill motor current draw, power consumption, feed rate, temperature, sound, battery life, and/or a position of the retracting enclosure.

In certain embodiments, a speaker configured to make an audible noise when a drill bit connected to the drill motor is through a first layer to avoid plunging. The first layer can be a cortical bone layer.

The retracting enclosure can be connected to a rack to slide the retracting enclosure between the retracted position and the extended position, the rack operatively connected to a pinion. The retracting motor can be operatively connected to a helical worm gear to rotate the helical worm gear, wherein the helical worm gear is operatively connected to the pinion such that when the helical worm gear rotates, the pinion is rotated thereby which, in turn, moves the rack linearly.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
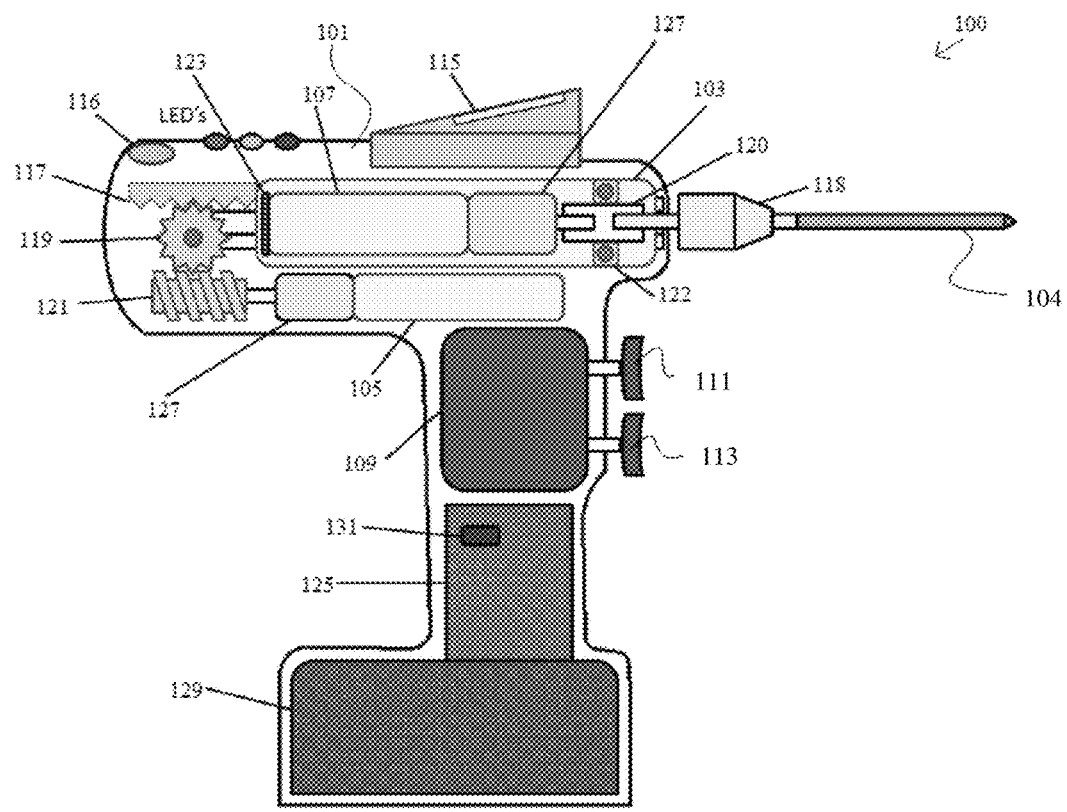
FIG. 1 is a side schematic of an embodiments of a surgical drill in accordance with this disclosure.
Figure 2A:
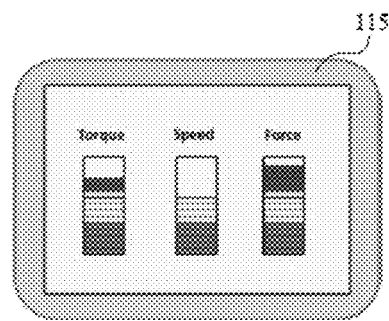
FIGS. 2A-2D are illustrative of embodiments of a feedback display in accordance with this disclosure.
Figure 2B:
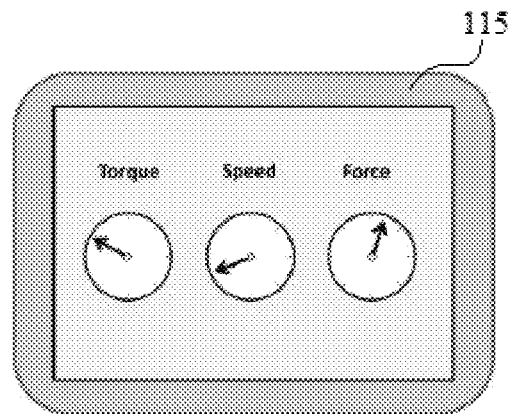
Figure 2C:
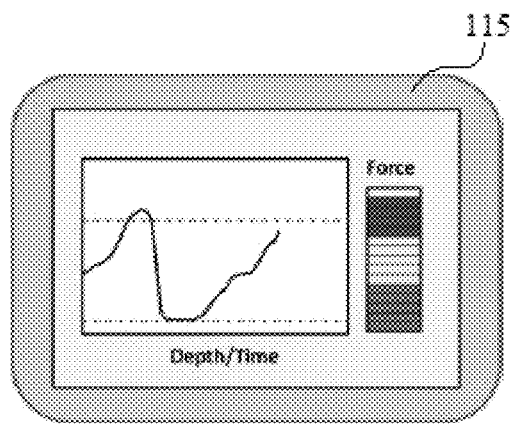
Figure 2D:
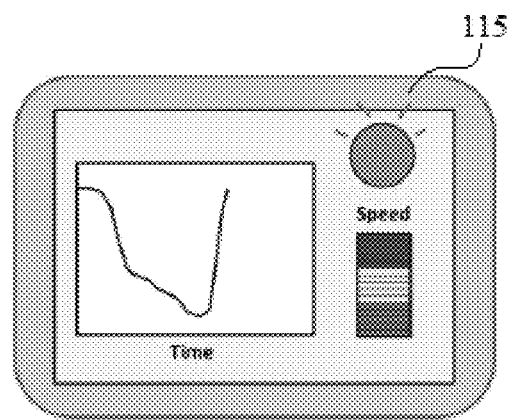

Reference will now be made to the drawings wherein like reference numerals identify similar structural features or aspects of the subject disclosure. For purposes of explanation and illustration, and not limitation, an illustrative view of an embodiment of a surgical drill in accordance with the disclosure is shown in FIG. 1 and is designated generally by reference character 100. Other embodiments and/or aspects of this disclosure are shown in FIGS. 2A-2D. The systems and methods described herein can be used to enhance safety and reduce clinician error during surgical drilling procedures.

In at least one aspect of this disclosure, referring to FIG. 1, a surgical drill 100 can include a housing 101, a retracting enclosure 103 slidably disposed within the housing 101 and configured to move between an extended position and a retracted position. The drill 100 includes a retracting motor 105 operatively connected to the retracting enclosure 103 to move the retracting enclosure 103 between the extended position and the retracted position.

The drill 100 can further include a drill motor 107 including a motor shaft (not shown) configured to connect to a drill chuck 118 and disposed within the retracting enclosure 103 such that the motor shaft can rotate relative to the retracting enclosure 103. The drill chuck 118 can be operatively coupled to the drill motor 107 and configured to selectively retain a drill bit 104. As shown, the chuck 118 can be connected to the drill motor 107 via a coupler 120 rotatably disposed within a bearing 122. The bearing 122 allows the coupler 120 and the chuck 118 to rotate relative to the retracting enclosure 103.

The motors 105 can include any suitable motor (e.g. a brushless DC electric motor) and can include and/or connect to a suitable gear box 127. As shown, at least one of the retracting motor 105 and/or the drill motor 107 can be operatively connected to a suitable gear box 127 for reducing the output speed and increasing torque of one or both of the motors 105, 107. It is also contemplated that one or both of the motors 105, 107 can be directly connected to their respective functional components (e.g., the worm gear 121, the drill chuck 118).

In certain embodiments, the drill 100 can include a trigger switch 109 configured to allow electrical energy to selectively flow to the retracting motor 105 and/or the drill motor 107. A forward drill trigger 111 can be operatively connected to the trigger switch 109. In certain embodiments, a reverse drill trigger 113 operatively connected to the trigger switch 109. The trigger switch 109 can be configured to activate the drill motor 107 in a first rotational direction when only the forward drill trigger 111 is actuated. The trigger switch can also be configured to activate the drill motor 107 in a reverse direction relative to the first rotational direction when only the reverse drill trigger 113 is actuated. In certain embodiments, when both the forward drill trigger 111 and the reverse drill trigger 113 are actuated simultaneously, the trigger switch 109 is configured to actuate the retracting motor 105 to move the retracting enclosure 103 from the extended position to the retracted position.

The reverse drill trigger 113 can be disposed above or below the forward drill trigger 111 such that a user can operate one trigger with an index finger and the other with a middle finger. This allows quick response to layer breakthrough to retract the drill bit to reduce/prevent plunging. Any other suitable configuration of trigger placement is contemplated herein.

It is contemplated that, instead of having both a forward drill trigger 111 and a reverse drill trigger 113, that the drill 100 can include a single drill trigger configured to activate the drill motor 107 in one or more rotation directions. In this case, if reverse motion is desired, a reverse switch can be included to switch to reverse. It is also contemplated that the drill 100 can include a separate retracting trigger configured to active the retracting motor 105 to move the retracting enclosure 103 from the extended position to the retracted position. The retracting trigger can be disposed above or below the forward drill trigger such that a user can operate one trigger with an index finger and the other trigger with a middle finger. Any other suitable configuration of trigger placement is contemplated herein.

The triggers and/or other related control systems as described herein can include variable current control such that the mount of applied current to the drill motor 107 can be varied based on the amount the drill triggers are actuated.

The drill 100 can include a feedback system including a feedback display 115 configured to display one or more parameters, graphs, gauges. The feedback display can include one or more suitable displays (e.g., one or more LCD screens, one or more LED's) to allow a clinician to easily interpret the information thereon. For example, LED's can relay information by changing color or blinking frequency.

Some embodiments of how the feedback display 115 can be configured are shown in FIGS. 2A-2D. Referring to FIGS. 2A-2D, the one or more parameters, graphs, and/or gauges can include drill motor torque, drill force, drill speed, time elapsed, depth verse time, drill motor current draw, power consumption, feed rate, temperature, sound, battery life, and/or a position of the retracting enclosure. For example, torque and speed can be measured through the drill motor 107 using known techniques.

In certain embodiments, a speaker 116 can be configured to make an audible noise when a drill bit 104 connected to the drill motor has penetrated through or is near penetrating through a first layer in order to avoid plunging. For example, in certain surgical procedures, the first layer can be a cortical bone layer. In certain embodiments, the speaker 116 can relay information by changing pitch or beep frequencies.

In certain embodiments, as shown in FIG. 1, the retracting enclosure 103 can be connected to a rack 117 to slide the retracting enclosure 103 between the retracted position and the extended position, the rack 117 being operatively connected to a pinion 119. The retracting motor 105 can be operatively connected to a helical worm gear 121 to rotate the helical worm gear 121. The helical worm gear 121 can be operatively connected to the pinion 119 such that when the helical worm gear rotates 121, the pinion 119 is rotated thereby which, in turn, moves the rack linearly 117 to move the retracting enclosure 103.

In certain embodiments, the retracting motor 105 can be configured to apply a force equal to or greater than a drill force to prevent the retracting enclosure 103 from moving due to drill force. In certain embodiments, a force sensor 123 can be operatively connected to the retracting enclosure 103 and/or the housing 101 in order to determine drill force. In this regards, the force sensor 123 can be connected to the feedback system which can be connected to a control board 125. The control board 125 can control electrical outputs to the retraction motor 107 in order to provide a correct amount of current to prevent the retracting enclosure 103 from sliding backward while the drill bit 104 is pressed against a drilling surface.

The control board 125 can also include the logic for the feedback system, the trigger switch 109, the drilling motor 107, and/or any other suitable function of the drill 100. The control board 125 can include any suitable hardware and/or software to perform the above functions.

The drill 100 can further include a battery 129 operatively connected to the drill motor 107 and/or the retracting motor 105 via any suitable selective electrical connection (e.g., through the trigger switch 109 and/or the control board 125). It is contemplated that any suitable source of electrical energy (e.g., a surgical generator) can be used to supply energy to the drill 100 in addition to or instead of a battery 129. A current sensor 131 can be included in electrical communication with the battery 129 or other power source to sense current draw for the feedback system.

The drill 100 and its attachments can be configured to be sterilizable (e.g., using autoclaving). The battery 129 can be removable and may not require sterilizing. The drill 100 can be configured to withstand the harsh steam autoclaving conditions (e.g., temperatures of 132° C. and higher at 30 psi). Cycles can typically last about 15 minutes, with 50 minutes of cooling time afterwards.

As described herein, a clinician can manually and safely perform surgical drilling operations with the herein disclosed devices. For example, in certain embodiments, when a clinician is about to break through a cortical bone layer, any suitable feedback mechanism can warn the clinician and the clinician can immediately activate the retracting motor 105 to retract the drill bit 104 back to the retracted position to avoid plunging. The clinician can reset the drill bit 104 to the extended position by deactivating the retraction motor through release of the triggers.

The methods and systems of the present disclosure, as described above and shown in the drawings, provide for surgical drills with superior properties including manually controllable retraction of the drill bit and feedback systems to enhance safety during a surgical procedure. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A surgical drill, comprising:
   a housing;
   a retracting enclosure slidably disposed within the housing and configured to move between an extended position and a retracted position;
   a retracting motor operatively connected to the retracting enclosure to move the retracting enclosure between the extended position and the retracted position;
   a drill motor including a motor shaft configured to connect to a drill chuck and disposed within the retracting enclosure such that the motor shaft can rotate relative to the retracting enclosure;
   a trigger switch configured to allow electrical energy to selectively flow to the retracting motor or the drill motor;
   a forward drill trigger operatively connected to the trigger switch;
   a reverse drill trigger operatively connected to the trigger switch, wherein the trigger switch is configured to activate the drill motor in a first rotational direction when only the forward drill trigger is actuated,
   wherein the trigger switch is configured to activate the drill motor in a reverse direction relative to the first rotational direction when only the reverse drill trigger is actuated,
   wherein when both the forward drill trigger and the reverse drill trigger are actuated simultaneously, the trigger switch is configured to actuate the retracting motor to move the retracting enclosure from the extended position to the retracted position.

2. The drill of claim 1, wherein the reverse drill trigger is disposed below the forward drill trigger such that a user can operate the forward drill trigger with an index finger and the reverse drill trigger with a middle finger.

3. The drill of claim 1, further comprising a feedback system including a feedback display configured to display one or more parameters, graphs, and/or gauges.

4. The drill of claim 3, wherein the one or more parameters, graphs, and/or gauges include drill motor torque, drill force, drill speed, time elapsed, depth verse time, drill motor current draw, power consumption, feed rate, temperature, sound, battery life, and/or a position of the retracting enclosure.

5. The drill of claim 1, further comprising a speaker configured to make an audible noise when a drill bit connected to the drill motor is through a first layer to avoid plunging.

6. The drill of claim 5, wherein the first layer is a cortical bone layer.

7. The drill of claim 1, wherein the retracting enclosure is connected to a rack to slide the retracting enclosure between the retracted position and the extended position, the rack operatively connected to a pinion.

8. The drill of claim 7, wherein the retracting motor is operatively connected to a helical worm gear to rotate the helical worm gear, wherein the helical worm gear is operatively connected to the pinion such that when the helical worm gear rotates, the pinion is rotated thereby which, in turn, moves the rack linearly.

9. The drill of claim 1, wherein the retracting motor is configured to apply a force equal to or greater than a drill force to prevent the retracting enclosure from moving due to drill force.

10. The drill of claim 1, wherein at least one of the retracting motor or the drill motor is operatively connected to a reduction gear box.

11. The drill of claim 1, further comprising a battery operatively connected to the drill motor and/or the retracting motor.

12. The drill of claim 1, further comprising a drill chuck operatively coupled to the drill motor, the drill chuck configured to selectively retain a drill bit.

* * * * *